US010806891B2

(12) United States Patent
Dib et al.

(10) Patent No.: US 10,806,891 B2
(45) Date of Patent: *Oct. 20, 2020

(54) METHOD FOR INFUSING STEM CELLS

(71) Applicant: Cook Regentec LLC, Indianapolis, IN (US)

(72) Inventors: Nabil Dib, Paradise Valley, AZ (US); Robert Edward Kohler, Lake Elmo, MN (US)

(73) Assignee: Cook Regentec LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/174,689

(22) Filed: Oct. 30, 2018

(65) Prior Publication Data
US 2019/0060611 A1 Feb. 28, 2019

Related U.S. Application Data

(60) Division of application No. 14/199,490, filed on Mar. 6, 2014, now Pat. No. 10,155,099, which is a
(Continued)

(51) Int. Cl.
*A61M 25/00* (2006.01)
*A61L 29/16* (2006.01)
(Continued)

(52) U.S. Cl.
CPC ......... *A61M 25/0023* (2013.01); *A61L 29/16* (2013.01); *A61M 25/0071* (2013.01);
(Continued)

(58) Field of Classification Search
CPC .......... A61M 25/0023; A61M 25/0071; A61M 25/0075; A61M 2005/1404;
(Continued)

(56) References Cited

U.S. PATENT DOCUMENTS 4,465,481 A   8/1984 Blake
4,608,984 A   9/1986 Fogarty
(Continued)

FOREIGN PATENT DOCUMENTS

EP   0 266 957 A2   5/1988
EP   0 318 918 A2   6/1989
(Continued)

OTHER PUBLICATIONS

Boekstegers, P. et al., "Myocardial gene transer by selective pressure-regulated retroinfusion of coronary veins," Gene Therapy 2000 7, pp. 232-240.
(Continued)

*Primary Examiner* — Theodore J Stigell
(74) *Attorney, Agent, or Firm* — Woodard, Emhardt, Henry, Reeves & Wagner, LLP

(57) ABSTRACT

A method for infusing a liquid into a patient's vasculature in accordance with an infusion protocol is disclosed. For this method, an infusion catheter having a multi-lumen infusion unit that is mounted adjacent the catheter's distal end is positioned in an artery within a predetermined distance from an intended target tissue surface. An inflation balloon is then deployed to at least partially occlude the artery and a force is exerted on the liquid to establish a flow rate for the liquid in the catheter. Specifically, the force is exerted to infuse the liquid from the catheter through the infusion unit and into the vasculature with a homogeneous distribution of the liquid to cover the intended surface of the target tissue. The flow rate can be established in accordance with an infusion protocol that is characterized by time and liquid volume parameters based on viscosity and pressure values in the liquid.

19 Claims, 7 Drawing Sheets

Related U.S. Application Data continuation-in-part of application No. 14/145,158, filed on Dec. 31, 2013, now Pat. No. 10,058,675, which is a continuation-in-part of application No. 13/473,988, filed on May 17, 2012, now Pat. No. 8,790,298, which is a continuation-in-part of application No. 12/563,876, filed on Sep. 21, 2009, now Pat. No. 8,647,311.

(51) Int. Cl.
| | | |
|---|---|---|
| *A61M 25/10* | (2013.01) | |
| *A61M 39/10* | (2006.01) | |
| *A61M 5/14* | (2006.01) | |
| *A61M 25/01* | (2006.01) | |
| *A61M 39/08* | (2006.01) | |

(52) U.S. Cl.
CPC ...... *A61M 25/0075* (2013.01); *A61L 2300/64* (2013.01); *A61L 2400/06* (2013.01); *A61M 25/1002* (2013.01); *A61M 39/105* (2013.01); *A61M 2005/1404* (2013.01); *A61M 2025/0183* (2013.01); *A61M 2025/1097* (2013.01); *A61M 2039/085* (2013.01); *A61M 2205/3334* (2013.01); *A61M 2206/18* (2013.01)

(58) Field of Classification Search
CPC ...... A61M 2025/0183; A61M 25/1002; A61M 2025/1097; A61M 39/105; A61L 29/16; A61L 2300/64; A61L 2400/06
See application file for complete search history.

(56) References Cited

U.S. PATENT DOCUMENTS

| | | | |
|---|---|---|---|
| 4,848,344 | A | 7/1989 | Sos et al. |
| 5,000,734 | A | 3/1991 | Boussignac et al. |
| 5,156,594 | A | 10/1992 | Keith |
| 5,328,470 | A | 7/1994 | Nabel et al. |
| 5,354,279 | A | 10/1994 | Hofling |
| 5,447,497 | A | 9/1995 | Sogard et al. |
| 5,447,797 | A | 9/1995 | Sogard et al. |
| 5,707,358 | A | 1/1998 | Wright |
| 5,913,842 | A * | 6/1999 | Boyd .................. A61B 17/29 604/28 |
| 5,964,223 | A | 10/1999 | Baran |
| 6,048,332 | A | 4/2000 | Duffy et al. |
| 6,293,920 | B1 | 9/2001 | Sweezer et al. |
| 6,312,374 | B1 | 11/2001 | von Hoffmann |
| 6,319,248 | B1 | 11/2001 | Nahon |
| 6,394,978 | B1 | 5/2002 | Boyle et al. |
| 6,500,145 | B1 | 12/2002 | Bicakci et al. |
| 6,524,302 | B2 | 2/2003 | Kelley |
| 6,579,287 | B2 | 6/2003 | Wittenberger et al. |
| 6,805,860 | B1 | 10/2004 | Alt |
| 7,686,781 | B2 | 3/2010 | Vinten-Johansen |
| 8,647,311 | B2* | 2/2014 | Dib .................. A61M 25/0023 604/103.11 |
| 8,790,298 | B2* | 7/2014 | Dib .................. A61M 25/0023 604/151 |
| 10,058,675 | B2* | 8/2018 | Dib ..................... A61M 25/10 |
| 10,155,099 | B2* | 12/2018 | Dib .................. A61M 25/0023 |
| 2002/0072647 | A1 | 6/2002 | Schock et al. |
| 2002/0188276 | A1 | 12/2002 | Evans et al. |
| 2003/0130610 | A1* | 7/2003 | Mager ................. A61M 1/3653 604/6.16 |
| 2003/0204171 | A1 | 10/2003 | Kucharczyk et al. |
| 2004/0138622 | A1 | 7/2004 | Palasis |
| 2005/0059930 | A1 | 3/2005 | Garrison et al. |
| 2005/0059931 | A1 | 3/2005 | Garrison et al. |
| 2005/0079161 | A1 | 4/2005 | Alt |
| 2005/0131386 | A1 | 6/2005 | Freeman et al. |
| 2005/0226855 | A1 | 10/2005 | Alt et al. |
| 2005/0287125 | A1* | 12/2005 | Morris ............... A61K 49/0452 424/93.7 |
| 2006/0004316 | A1 | 1/2006 | Difiore et al. |
| 2006/0030814 | A1 | 2/2006 | Valencia et al. |
| 2006/0074399 | A1 | 4/2006 | Bates |
| 2007/0106208 | A1 | 5/2007 | Uber et al. |
| 2008/0039786 | A1 | 2/2008 | Epstein et al. |
| 2009/0157042 | A1 | 6/2009 | Cheng et al. |
| 2009/0192450 | A1 | 7/2009 | Miesel et al. |
| 2009/0209630 | A1 | 8/2009 | Coleman et al. |
| 2010/0004593 | A1 | 1/2010 | Gregorich et al. |
| 2010/0010474 | A1 | 1/2010 | Bates |
| 2010/0210927 | A1 | 8/2010 | Gillies et al. |
| 2010/0234804 | A1 | 9/2010 | Hiejima et al. |
| 2011/0046542 | A1 | 2/2011 | Evans et al. |
| 2011/0071496 | A1 | 3/2011 | Dib |
| 2011/0105960 | A1 | 5/2011 | Wallace |
| 2011/0270131 | A1 | 11/2011 | Snow et al. |
| 2011/0295114 | A1 | 12/2011 | Agah et al. |
| 2011/0295302 | A1 | 12/2011 | Mohl |
| 2011/0319917 | A1 | 12/2011 | Ferrera et al. |
| 2012/0035595 | A1 | 2/2012 | Goedje et al. |
| 2012/0041359 | A1 | 2/2012 | Schoenle et al. |
| 2012/0148668 | A1 | 6/2012 | Consigny et al. |
| 2012/0226225 | A1* | 9/2012 | Dib .................. A61M 25/0023 604/84 |
| 2012/0245521 | A1 | 9/2012 | Gulachenski et al. |
| 2013/0338637 | A1 | 12/2013 | Fischer, Jr. et al. |
| 2014/0114239 | A1 | 4/2014 | Dib et al. |
| 2014/0207107 | A1 | 7/2014 | Dib et al. |
| 2017/0073309 | A1 | 3/2017 | Fischer, Jr. et al. |

FOREIGN PATENT DOCUMENTS

| | | |
|---|---|---|
| EP | 0 761 252 A1 | 3/1997 |
| EP | 2 389 973 A1 | 11/2011 |
| EP | 2 389 974 A1 | 11/2011 |
| JP | S62-122675 | 6/1987 |
| JP | S63-177868 | 7/1988 |
| JP | H08-38607 | 2/1996 |
| JP | H09-70441 | 3/1997 |
| JP | H11-504233 | 4/1999 |
| JP | H12-300524 | 10/2000 |
| JP | 2002-543868 | 12/2002 |
| JP | 2005-194272 | 7/2005 |
| JP | 2007-175497 | 7/2007 |
| JP | 2009-522010 | 6/2009 |
| JP | 2009-524442 | 7/2009 |
| JP | 2011-245300 | 12/2011 |
| WO | WO 1995/005868 | 3/1995 |
| WO | WO 1996/012518 A1 | 5/1996 |
| WO | WO 1996/33756 | 10/1996 |
| WO | WO 1998/048884 A3 | 11/1998 |
| WO | WO 1999/025421 A1 | 5/1999 |
| WO | WO 2000/067647 A1 | 11/2000 |
| WO | WO 2001/034208 A1 | 5/2001 |
| WO | WO 2006/078884 A3 | 7/2006 |
| WO | WO 2008/020967 A2 | 2/2008 |
| WO | WO 2008/057370 A3 | 5/2008 |
| WO | WO 2011/035182 A2 | 3/2011 |
| WO | WO 2013/173166 A1 | 11/2013 |
| WO | WO 2013/184782 A3 | 12/2013 |
| WO | WO 2015/102820 A3 | 7/2015 |

OTHER PUBLICATIONS

English Machine Translation of JP 2009-522010 A.
Inter Search Rpt and Written Opinion—PCT/US2013/044287.
Invitation to Pay Additional Fees and Partial International Search Report issued in PCT/US2013/044287, dated Sep. 23, 2013.
Lee, Richard et al., "Retrograde Infusion of Lidocaine or L-Arginine Before Reperfusion Reduces Myocardial Infarct Size," Annals of Thoracic Surg. Assn. 1998.
Murad-Netto, Stans et al., "Stem Cell Therapy with Retrograde Coronary Perfusion in Acute Mocardial Infarction. A New Technique," arquivos Brasileiros de Cardiologia, vol. 83, No. 4, Oct. 2004, pp. 352-354.

(56) References Cited

OTHER PUBLICATIONS

Nabel, Elizabeth et al., "Gene Transfer and Cardiovascular Disease," TCM Jan.-Feb. pp. 12-17.
Nabel, Elizabeth et al., "Recombinant Gene Expression in Vivo Within Endothelial Cells of the Arterial Wall," Science, vol. 244 pp. 1342-1344.
Nabel, Elizabeth et al., "Safety and Toxicity of Catheter Gene Delivery to the Pulmonary Vasculatore in a Patient with Metastatic Melanoma," Human Gene Therapy 5:1089-1094 Sep. 1994.
Shinmura, Ken et al., "Catheter-Delivered In Vivo Gene Transfer into Rat Myocardium Using the Fusigenic Liposomal Mediated Method," Jpn Heart J 2000; 41: 633-647.
Stauer—Internet pages, "German cardiologist conducts first intracoronary stem cell transplantation," Stem cell therapy in MI patient, http://www.theheart.org/article/185323 last printed Jun. 6, 2011.
Suzuki, Ken et al., "Development of a Novel Method for Cell Transplantation Through the Coronary Artery," Circulation 2000; 102;III-359-III-364.
Suzuki, Ken et al., "Targeted Cell Delivery Into Infarcted Rat Hearts by Retrograde Intracoronary Infusion: Distribution, Dynamics, and Influence on Cardiac Function," Circulation 2004;110;II-225-II-230.
Taylor, Doris A. et al., "Delivery of Primary Autologous Skeletal Myoblasts into Rabbit Heart by Coronary Infusion: A Potential Approach to Myocardial Repair," Proceedings of the Assn of Am Physicians, vol. 109, No. 3, pp. 245-253.
Translation of Office Action dated Apr. 28, 2015 in related JP Application No. 2012-529945.
English Machine Translation of JP 2000300524.
English Machine Translation of JP 2002543868.
English Machine Translation of JP 2005194272.
English Machine Translation of JP 2007175497.
English Machine Translation of JP 2009524442.
English Machine Translation of JP H11-504233.
English Machine Translation of JP2011245300.
English Machine Translation of JP62122675.
Written Opinion issued for Application No. 11201407429P dated Aug. 28, 2015.

* cited by examiner

METHOD FOR INFUSING STEM CELLS

This application is a divisional of application Ser. No. 14/199,490 filed Mar. 6, 2014, which is a continuation-in-part of application Ser. No. 14/145,158 filed Dec. 31, 2013 which issued as U.S. Pat. No. 10,058,675 which issued on Aug. 26, 2018, and which is a continuation-in-part of application Ser. No. 13/473,988 filed May 17, 2012 which issued as U.S. Pat. No. 8,790,298 which issued on Jul. 29, 2014, and which is a continuation-in-part of application Ser. No. 12/563,876, filed Sep. 21, 2009, which issued as U.S. Pat. No. 8,647,311 on Feb. 11, 2014. The contents of application Ser. No. 14/145,158, application Ser. No. 13/473,988 and U.S. Pat. No. 8,647,311 are each incorporated by reference herein.

FIELD OF THE INVENTION

The present invention pertains generally to infusion systems for introducing particles into a fluid stream. More particularly, the present invention pertains to infusion systems for introducing (infusing) particles of biological matter (e.g. stem cells) into the vasculature of a patient without diminishing the therapeutic effectiveness of the biological matter. The present invention is particularly, but not exclusively useful as a system using a multi-lumen filter that allows particles to enter a lumen of the separator, either individually or in small groupings, for subsequent infusion into the vasculature of a patient.

BACKGROUND OF THE INVENTION

An introduction of particles into the vasculature of a patient requires simultaneously satisfying several different concerns or considerations. Depending on the type of particles involved, a concern of significant importance involves preventing the particles from flocculating, i.e. clumping together, as they are being infused or introduced into the vasculature. This is of particular concern in the case of stem cells which can flocculate, but which are most effective in therapy if left to function either as individual cells or in small groups of cells. An additional benefit of preventing particles from flocculating is the prevention of heart attacks which may be caused when clumps of cells are introduced into the coronary circulatory system. Also, it is possible that the retention rate of stem cells in the heart, or other targeted tissue, will increase when the stem cells are infused while blood flow is slow in the circulatory system.

In all types of intravascular therapy (i.e. intracoronary, intra-arterial or intravenous), it is always an essential concern that the therapeutic agent (e.g. biologics or drugs) be infused or delivered in a predictably controlled manner. Furthermore, it is important that the therapeutic agent be effectively delivered to a proper destination in the vasculature. All of this involves dosage and delivery rate considerations. Moreover, it requires careful handling of the therapeutic agent to insure it (the therapeutic agent) is not damaged or otherwise compromised during an infusion.

From a mechanical perspective, it is known that the diameter of a fluid passageway is a factor that will affect the rate of fluid flow through the passageway. For protocols where small groups of de-flocculated particles are to be infused into a vessel of a vasculature, the diameter of the passageway must obviously be large enough to individually accommodate the small groups of particles. On the other hand, it must also be small enough to separate and prevent larger groups of particles (cells) from clinging to each other. A consequence of this is that the rate at which particles can be carried through the passageway will be circumscribed by the dimensions of the passageway. A further consequence of this is that, as particles leave the passageway, they are then influenced by the flow of fluid (i.e. blood) in the vessel of the vasculature. Depending on the purpose of the protocol, this may mean that the downstream fluid flow in the vasculature will somehow also need to be regulated.

In some cases, the downstream fluid flow in the vasculature (discussed above) can be controlled or regulated using an inflatable balloon that is attached to an outside surface of the catheter tube. For these and similar arrangements, when the balloon is deployed at the treatment site (i.e. inflated), a pressure is exerted on the catheter tube. The catheter tube, however, is typically made of a flexible material to allow it to twist and turn as the catheter is navigated through the patient's vasculature. Because of the flexible nature of the catheter tube, it is typically susceptible to kinking and/or collapse during inflation of the balloon. This can be particularly troublesome for infusion catheters where the material to be infused is pumped through a central lumen of the catheter tube. In this instance, a collapse or even partial blocking of the central lumen where the balloon is inflated can impede fluid flow in the central lumen, and adversely affect an infusion procedure. In addition to reducing flow, a collapsed or blocked catheter tube lumen can reduce cell viability during transport through the lumen by exposing the cells to shear stress (Note: in some cases, viability has been found to be lowered by around 70-80% when flow is impeded in the central lumen).

For each type of cell or cell family, there is a shear stress threshold which must be avoided to prevent cell injury. For some types of cells, exposure to stresses above a maximum shear stress is sufficient to avoid damage. For other types of cells, both the magnitude of the shear stresses and the time the cell is exposed to the shear stress must be considered when establishing the shear stress threshold.

A number of factors can influence the shear stress levels that develop when a fluid medium having a suspension of cells is pumped through an infusion catheter and introduced into the vasculature of a patient. These factors can include the size and geometry of the internal passages in the catheter, the concentration and type of cells present in the fluid medium and the flow rate. For example, the use of a multi-lumen separator in an infusion catheter can, in some cases, affect the levels of shear stress that are developed within the catheter. In addition, as described above, the use of an inflation balloon can in some cases, affect the size and geometry of the internal passages in the catheter, which in turn, can affect the levels of shear stress that are developed.

In light of the above, it is an object of the present invention to provide an infusion system that can effectively introduce only small groups of particles into a fluid flow. Another object of the present invention is to provide an infusion system that coordinates the flow rate of a particle/fluid medium (i.e. a first fluid) with the flow rate of a fluid (i.e. a second fluid) into which the particle/fluid medium is being introduced. Still another object of the present invention is to provide an infusion system that produces a low exit pressure to reduce the impact on a vessel wall caused when fluid exits a catheter and enters the vessel. It is still another object of the present invention to provide an infusion system having a balloon to regulate blood flow at an infusion site that is not subject to central lumen collapse or blocking during balloon inflation. It is yet another object of the present invention to provide an infusion protocol which ensures that stresses exerted on an infusion fluid are maintained below a shear stress threshold specified for the type of cells present in the infusion fluid to prevent cell damage during an infusion procedure. It is another object of the present invention to provide a method for determining suitable influsion flow rates and fluid medium cell concentrations for a particular catheter size and geometry that will ensure that stresses exerted on an infusion fluid are maintained below a shear stress threshold specified for the type of cells present in the infusion fluid to prevent cell damage during an infusion procedure. Yet another object of the present invention is to provide a method for infusing stem cells that is easy to use, is simple to implement and is comparatively cost effective.

SUMMARY OF THE INVENTION

In accordance with the present invention, an infusion system includes an elongated catheter which is formed with a central lumen that extends between the proximal and distal ends of the catheter. Preferably, the catheter is tubular shaped with a smooth, circular, outer surface and, for purposes of description, the catheter defines a longitudinal axis. A source of a fluid medium having particles suspended therein (i.e. a particle/fluid medium) is connected in fluid communication with the proximal end of the catheter, and a separator is connected at the distal end of the catheter. For purposes of the present invention, the separator is provided to prevent the particles from flocculating as they are infused or introduced into a vessel in the vasculature of a patient. As envisioned for the present invention, the particles can be either biologics (i.e. cell, gene or protein) or drugs. And, they can be introduced into the vasculature for intracoronary, intra-arterial, or intravenous therapy.

Structurally, the separator is formed with a plurality of parallel lumens. Thus, with the separator affixed to the distal end of the catheter, each lumen of the separator is individually placed in fluid communication with the central lumen of the catheter. Importantly, each individual lumen is dimensioned to sequentially receive only small groups of particles (i.e. less than ten) therethrough. Specifically, although each lumen can receive several particles at a time, each lumen is sufficiently small to effectively separate particles from clinging to each other as they are received into the lumen. It follows that the system also includes a means for moving the particle/fluid medium through the lumen of the catheter, for further movement of the particles in alignment through individual lumens of the separator. For purposes of the present invention the means for moving this particle/fluid medium can be any such means well known in the pertinent art, such as an IV pole, a syringe, or a pump.

In addition to the separator described above, the system of the present invention also includes a configurable (inflatable) valve, such as a balloon. Specifically, the configurable valve is positioned on the outer surface of the catheter to surround the catheter at a location that is proximal to the separator. Further, the valve is formed with a plurality of apertures that are arranged around the axis of the catheter. The purpose of these apertures is to control the axial movement of a fluid (e.g. blood) past the catheter in a distal direction substantially parallel to the axis of the catheter. This control is preferably provided by an inflator that selectively constricts the apertures of the valve to control the flow rate of fluid through the apertures.

In a preferred embodiment of the present invention, the valve is formed as an annulus that is centered on the axis. With this structure, the annulus has an inner diameter that is affixed to the outer surface of the catheter. The valve also has a substantially non-compliant material positioned on the outer periphery of the annulus that maintains the outer diameter at a predetermined radial distance from the catheter when the valve is inflated into a base configuration. As mentioned previously, the valve can be a balloon as commonly used in the pertinent art, and the balloon can be of any material appropriate for this type of procedure. As examples, the balloon may be nylon, polyethylene, or polyethylene terephthalate (PET). Aside from the non-compliant material, the rest of the annulus is made of a compliant material. Importantly, this compliant material is responsive to the inflator to selectively constrict the apertures. Thus, in operation, an additional inflation of the valve beyond its base configuration substantially maintains the outer diameter at the predetermined radial position, while incrementally constricting the apertures.

Additional features of the present invention include a provision for positioning the catheter in the vasculature over a monorail type guide wire. Also, a fluid flow controller can be provided to meter fluid flow from the source into the central lumen of the catheter at a selected fluid pressure.

Within the context of the present invention, several structural variations are envisioned that will facilitate the infusion of biologics into the vasculature of a patient. These variations can also enhance the diffusion and retention rate of the stem cells, drugs, proteins, or particles by the heart. These include: 1) the creation of a recollection chamber at the distal end of the catheter for establishing a safe and effective fluid infusion velocity for the biologics; 2) the orientation of the proximal (upstream) surface of a separator that will promote separation of biologics from each other prior to their infusion; and 3) an inflatable balloon that will coordinate and control blood flow through the vasculature in cooperation with the infusion of biologics. One additional variation is the use of a venous catheter in place of the catheter disclosed previously.

A recollection chamber used during an intravenous or an arterial infusion is provided at the distal end of the catheter and is created by positioning the separator in the central lumen of the catheter at a distance d from the distal end of the catheter. With this positioning, the recollection chamber will be substantially tubular, it will have a length d, and it will have a diameter the same as that of the central lumen. It should be noted that the valve, or balloon, does not extend to this location near the distal end of the catheter.

Insofar as structural variations of the separator are concerned, in an alternate embodiment of the separator disclosed above, the proximal (upstream) surface is slanted at an angle $\alpha$ relative to the axis of the catheter. Preferably, the angle $\alpha$ will be around 60°, with a consequence that the lumens established by the separator will have different lengths. In one version, the proximal (upstream) surface of the separator will be flat, with the entrance to each lumen angled at the angle $\alpha$ from the axis of the catheter. In another version, this surface will have a stepped configuration so that the entrance to each lumen will be perpendicular to the axis of the catheter. For both versions, the distal (downstream) surface of the catheter will be perpendicular to the axis of the catheter.

In combination, the separator and the recollection chamber function to promote and maintain the separation of biologics as they are being safely infused. In particular, the recollection chamber slows the fluid velocity rate of the infusion fluid, after it has been accelerated through the separator. To further maintain safe fluid flow through the vasculature, an inflatable balloon can be attached to the outer surface of the catheter and it can be selectively inflated to coordinate the respective rates of blood flow and fluid infusion.

In another aspect of the present invention, a reinforcing member is employed to strengthen the catheter wall under the inflatable balloon. With this arrangement, the catheter does not kink or collapse due to the pressure exerted on the catheter wall when the balloon is inflated. Instead, a substantially constant cross-section for the central lumen is maintained during an inflation of the balloon, allowing for the unimpeded flow of particles to pass through the central lumen during an infusion of particles into a patient's vasculature.

In more structural detail, for this embodiment, the reinforcement member is positioned in contact with a section of the catheter wall that encircles a portion of the central lumen. Specifically, the reinforcement member is positioned in contact with the catheter wall under the inflatable balloon.

In one embodiment, the reinforcement member comprises an annular shaped ring that is affixed to the outer surface of the catheter wall under the inflatable balloon. With the annular shaped ring affixed, the ring is oriented substantially perpendicular to a longitudinal axis defined by the infusion catheter and concentric with the axis, to strengthen the catheter wall.

In another embodiment, a separator (as described above) acts as both a filter and the reinforcement member. For this embodiment, the separator is located under the inflatable balloon and positioned in contact with the inner surface of the wall. Thus, the separator provides the dual function of preventing particles from flocculating as they are infused into the vasculature and functions to strengthen the catheter wall to prevent collapse during balloon inflation.

In another aspect of the present invention, a method for infusing a liquid into the vasculature of a patient includes the steps of supplying a source of the liquid and providing an infusion catheter. For this aspect, the infusion catheter has a proximal end and a distal end and is formed with a multi-lumen infusion unit mounted adjacent the distal end of the infusion catheter. In addition, the infusion catheter includes an inflation balloon that is affixed to the catheter at a location that is proximal to the multi-lumen infusion unit.

For this method, the distal end of the inflation catheter is positioned in an artery of the vasculature of the patient at a location within a predetermined distance from an intended target tissue surface. With the inflation catheter positioned, the balloon is inflated to at least partially occlude the artery. Next, a force is exerted on the liquid to establish a flow rate for the liquid in the catheter. Specifically, the force is exerted to infuse the liquid from the catheter through the infusion unit and into the vasculature with a homogeneous distribution of the liquid to cover the intended surface of the target tissue.

Importantly for this method, the flow rate can be established in accordance with an infusion protocol that is characterized by time and liquid volume parameters based on viscosity and pressure values in the liquid. For example, the force can be exerted on the liquid in accordance with the infusion protocol to provide a substantially constant shear-stress distribution in the liquid during an infusion. In addition, the force can be exerted on the liquid in accordance with the infusion protocol to provide a substantially homogeneous distribution of elements suspended in the liquid during an infusion.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
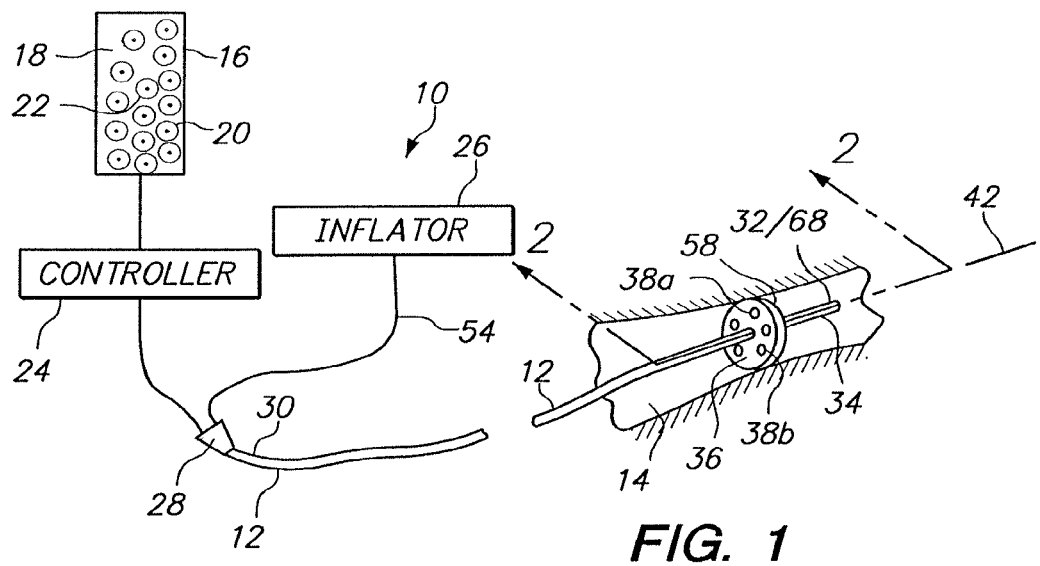
FIG. 1 is a schematic/perspective view of the system of the present invention shown with the system catheter positioned in an operational environment.

Referring initially to FIG. 1 a system for introducing (infusing) a fluid in accordance with the present invention is shown and is generally designated 10. As shown, the system 10 includes a catheter 12 that can be advanced into a vessel 14 to position the catheter 10 at a predetermined location in the vasculature of a patient (not shown). For the purposes of the present invention, the vessel 14 is preferably an artery or a vein in the cardiovascular system of a patient, and the system 10 is used for an intra-arterial, intravenous or intra-coronary protocol.

In detail, FIG. 1 shows that the system 10 includes a source 16 for holding a fluid medium 18. As also shown in FIG. 1, a plurality of particles 20 are suspended in the fluid medium 18 to create a particle/fluid medium 22. For the present invention, the particles 20 may be some form of a drug or, most likely, they will be some form of a biologics (i.e. cell, gene or protein). In any event, the particles 20 will be suspended in the particle/fluid medium 22 for transport from the source 16 through the system 10 and into the vessel 14. As mentioned above for the system 10, the source 16 can be a syringe of a type well known in the pertinent art. FIG. 1 also shows that the system 10 includes a controller 24 that is in fluid communication with the source 16. As envisioned for the present invention, the controller 24 can be any type device that is known in the pertinent art for moving a fluid (e.g. the particle/fluid medium 22) through a fluid flow system (e.g. system 10). In general, such a device may be an IV pump, an IV pole, a syringe, or some other fluid flow metering apparatus. For an embodiment of the system 10 wherein the source 16 is a syringe, however, there is no specific need for a controller 24.

FIG. 1 also shows that the system 10 includes an inflator 26 for a purpose to be discussed below. When both the controller 24 and the inflator 26 are used for the system 10, they can be individually joined at a connector 28 to, respectively, establish separate fluid communication channels with the catheter 12. Preferably, as shown, this connector 28 is connected in fluid communication with the proximal end 30 of the catheter 12.

Still referring to FIG. 1, it is seen that the system 10 includes a tip (filter) 32 (hereinafter sometimes also referred to as a separator 68) that is affixed to the distal end 34 of the catheter 12. Further, it is seen that a valve 36 is mounted on the catheter 12 proximal the distal end 34, and that the valve 36 is formed with a plurality of apertures, of which the apertures 38a and 38b are exemplary. The actual construction of the distal portion of the catheter 12, and the cooperation of structure between the separator 68 and the valve 36 will perhaps be best appreciated with reference to FIG. 2.

Figure 2:
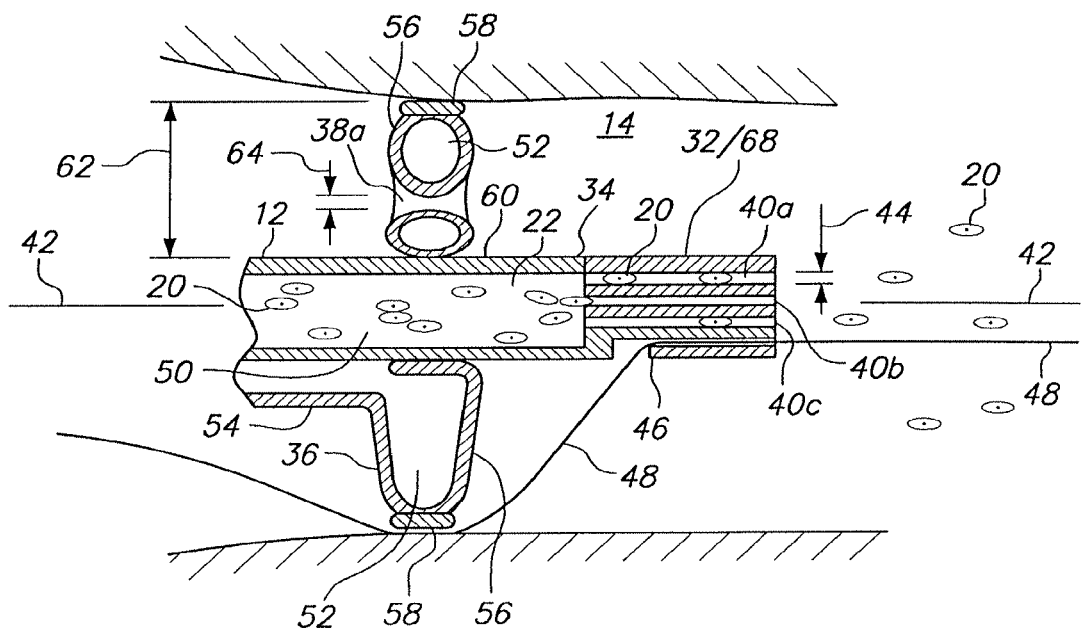
FIG. 2 is a cross-section view of the separator and distal portion of the system catheter as seen along the line 2-2 in FIG. 1.

Referring to FIG. 2, and with specific reference to the separator 68, it will be seen that the separator 68 is formed with a plurality of lumens, of which the lumens 40a, 40b, and 40c are exemplary. More specifically, the lumens extend axially through the separator 68 and are substantially parallel to each other. They are also substantially parallel to the axis 42 that is generally defined by the catheter 12. Importantly, each lumen is established with a diameter 44 that is specifically dimensioned to receive only individual or small groups of particles 20. Although each lumen can receive several de-flocculated particles 20 at a time, the individual particles 20 or small groups of particles remain separated while they transit the lumen (e.g. see lumen 40a). Further, the separator 68 can be formed with a monorail lumen 46 that will interact with a guide wire 48, in a manner well known by the skilled artisan, for the purpose of positioning the catheter 12 within the vessel 14.

With the structure of the separator 68 in mind, as described above, it is an important aspect of the present invention that the diameter 44 of each lumen be dimensioned to prevent the entry of large groups of flocculated particles 20 into the lumen from the central lumen 50 of the catheter 12. In particular, for different therapeutic protocols, it may be very necessary that the particles 20 be dispersed as they enter the vessel 14, to thereby minimize the possibility of subsequent flocculation in the vessel 14, which may lead to heart attack or stroke if the cells are infused into the coronary circulatory system. Further, dispersion of the particles 20 as they enter the vessel 14 will provide better mixing with the blood for more efficient distribution to tissue.

Recall, the valve 36 is formed with a plurality of apertures. Further, with cross reference to FIG. 1 and FIG. 2, it will also be appreciated that, when inflated, the valve 36 is generally shaped as an annulus and is formed with an inflation chamber 52. As shown, the inflation chamber 52 is connected in fluid communication with the inflator 26 via an inflation line 54. Within this structure, the inflation line 54 can be integrated into the catheter 12. For operational purposes, the valve 36 includes a valve body 56 that is made of a compliant, inflatable material. The valve 36 also includes a rim 58 made of a substantially non-compliant material that is located on the periphery of the annulus shaped valve 36. For the system 10, the valve 36 is located proximal to the separator 68, and it is affixed to the outer surface 60 of the catheter 12 by any means known in the pertinent art, such as by gluing or bonding.

Operationally, the valve 36 (balloon) starts from a deflated configuration, and it is then inflated by the inflator 26 into a base configuration (see FIGS. 1 and 2) wherein the valve 36 is constrained by the rim 58. In this base configuration, the valve 36 will extend from the surface 60 of catheter 12 through a radial distance 62 and, in the base configuration, it will most likely make contact with the vessel 14. Also, in the base configuration, each aperture (e.g. aperture 38a) will have a diameter 64. With an additional inflation of the valve 36 by the inflator 26, however, two different structural consequences occur. For one, the rim 58 does not expand from the base configuration. Thus, the radial distance 62 remains substantially constant. For another, the valve body 56 will expand in response to the inflator 26 such that the apertures are incrementally constricted. Stated differently, and with specific reference to the aperture 38a, the diameter 64 will be diminished. In an alternate embodiment for the present invention, there may be no need for the valve 36.

For an operation of the system 10 in an intra-arterial, intravenous or intracoronary protocol, a guide wire 48 is first prepositioned in the vasculature of a patient. The guide wire 48 is then received into the monorail lumen 46 of the catheter 12, and the catheter 12 is advanced over the guide wire 48 and into position in the vasculature of the patient. Once the catheter 12 has been properly positioned, the valve 36 is inflated into its base configuration, or beyond. The exact extent of inflation for valve 36 will depend on the desired flow rate for fluid through the apertures in the vessel 14. With the valve 36 inflated, the controller 24 is then activated to cause a flow of particle/fluid medium 22 from the source 16 and through the central lumen 50 of the catheter 12. As particles 20 in the particle/fluid medium 22 arrive at the separator 68, the respective diameters 44 of individual lumens in the separator 68 allow only individual particles 20 or small groups of particles 20 to enter the lumen. Thus, the flocculation of particles 20 in the central lumen 50 is disrupted, and flocculation of the particles 20 after they have passed through the separator 68 is minimized. Although the above discussion has focused on applications of the system 10 within the cardiovascular system of a patient, the system 10 is appropriate for any use wherein particles 20 may be suspended in a particle/fluid medium 22 for subsequent release as individual particle 20 into a fluid flow (e.g. blood flow through a vessel 14).

Figure 3:
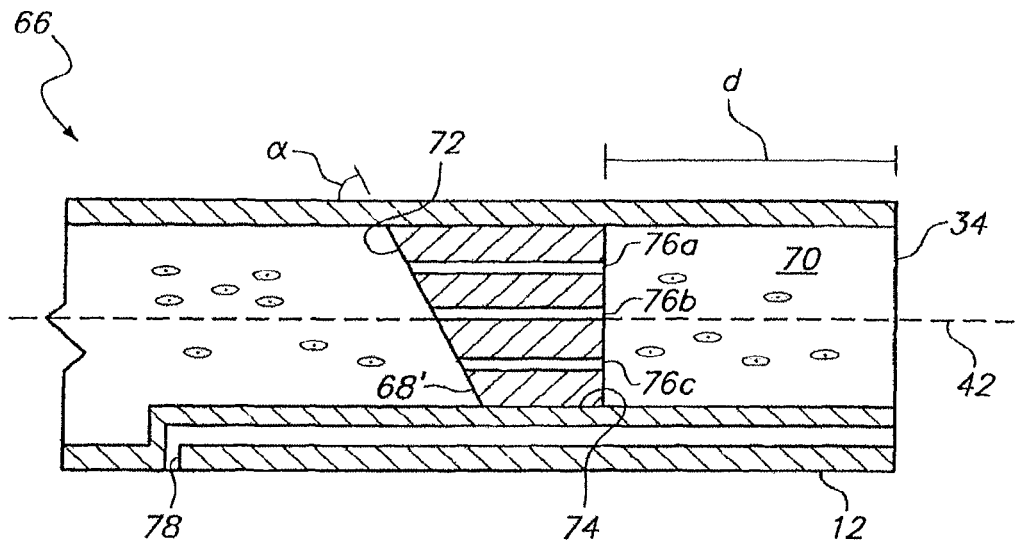
FIG. 3 is a cross-section view of an alternate embodiment of the infusion tip as seen along line 2-2 in FIG. 1.

Referring to FIG. 3, an infusion tip for biologics is shown and generally is designated 66. In this embodiment, a separator 68' is located in the central lumen 50 of the catheter 12 at a distance d from the distal end 34 of the catheter 12. As so located, the separator 68' creates a recollection chamber 70 having a length d at the distal end 34 of the catheter 12. Specifically, the recollection chamber 70 is a tubular section formed onto the distal end 34 of the catheter 12. If necessary, the recollection chamber 70 may be established by a stand-alone piece of tubing that can be attached to the distal end 34 of the catheter 12.

Still referring to FIG. 3, it is seen that the separator 68' has a proximal (upstream) surface 72 and a distal (downstream) surface 74. In detail, the proximal surface 72 of the separator 68' is oriented at a slant angle α relative to the axis 42 of the catheter 12. The distal surface 74 of the separator 68', however, is perpendicular to the axis 42, and it is substantially flat. Keeping in mind the structure disclosed above, a consequence of the slanted proximal surface 72 is that the proximal end of each lumen 76a-c will also be slanted at angle α relative to the axis 42 of catheter 12. Consequently, when fluid flows through the catheter 12 and encounters the slanted proximal surface 72 of the catheter 12, it is redirected to flow through the lumens 76a-c of the separator 68'. In operation, this redirection helps prevent particles 20 in the fluid from flocculating prior to entering the vasculature of the patient. Upon exiting the lumens 76a-c of the separator 68', the fluid enters the recollection chamber 70 where it is allowed to slow down before entering the vasculature of the patient.

Figure 4:
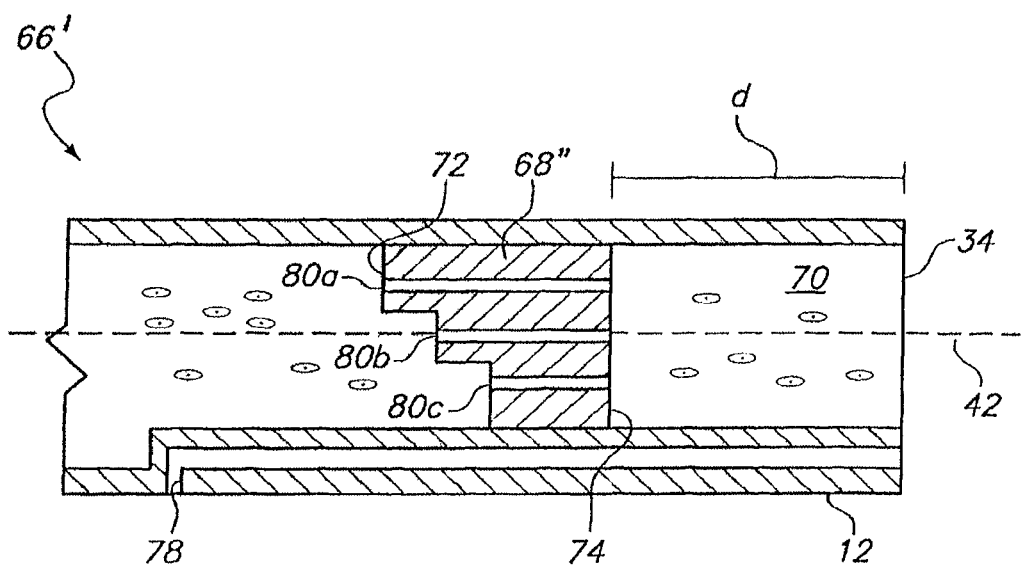
FIG. 4 is a cross-section view of an alternate embodiment of the infusion tip shown in FIG. 3.

For embodiments shown in FIGS. 3 and 4, the guide wire exit lumen 78 is formed onto the catheter 12 at a location approximately 25-30 millimeters proximal the separator 68' and 68".

Referring now to FIG. 4, a variation of the infusion tip 66' is shown wherein the proximal surface 72 of the separator 68" is formed with a step configuration. Due to the step configuration, the proximal end of each lumen 80a-c remains substantially perpendicular to the axis 42 of the catheter 12. Thus, in all important respects, the infusion tips 66, 66' shown in FIGS. 3 and 4, respectively, are the same with the exception that the proximal surfaces differ. It should be noted that the proximal surface 72 of the separator 68 can also take the shape shown in FIG. 2 for the separator 32/68.

Figure 5A:
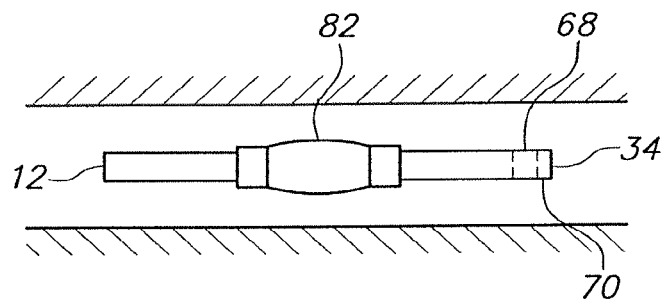
FIG. 5A is a plan view of the balloon of the present invention in a deflated configuration and shown with the catheter positioned in an operational environment.
Figure 5B:
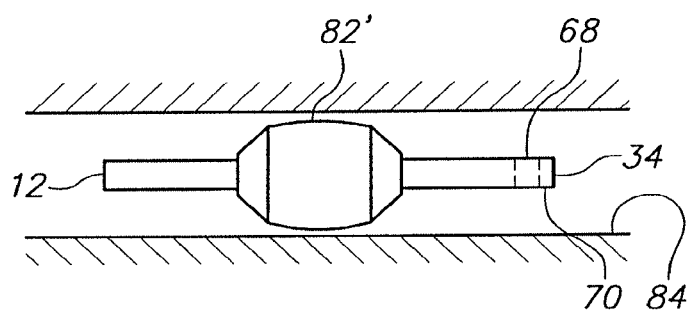
FIG. 5B is a plan view of the balloon of the present invention in an inflated configuration and shown with the system catheter positioned in an operational environment.

Referring now to FIG. 5A and FIG. 5B, a selectively inflatable balloon 82 is shown attached to the catheter 12 at a location proximal the separator 68. When inflated as shown in FIG. 5B, the balloon 82' controls the flow rate of blood around the catheter 12 by expanding radially away from the catheter 12 towards the vessel wall 84. As envisioned for the present invention, the flow rate of the blood outside the catheter 12 should be compatible with the flow rate of fluid inside the catheter 12 in order to minimize turbulence at the distal end 34 of the catheter 12. In any event, the overall objective for the recollection chamber 70 and the inflatable balloon 82 is to decrease the probability of damage or injury to the vasculature of the patient during an infusion by decreasing the flow rate of blood to allow particles additional time to diffuse and to travel through blood vessels and into the tissue to be treated.

Figure 6:
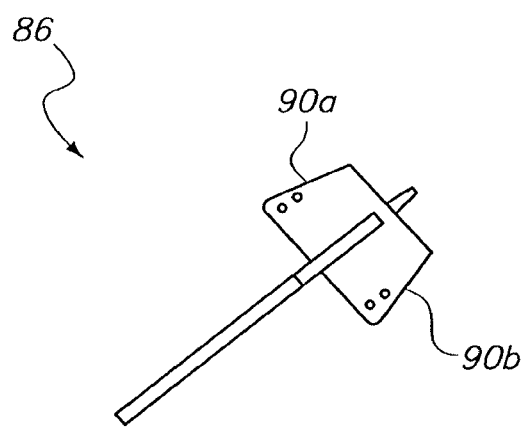
FIG. 6 is a plan view of the venous catheter for the present invention.

Referring now to FIG. 6, it is to be appreciated that an infusion tip 66 in accordance with the present invention can be employed in a venous catheter 86 of a type that is well-known in the pertinent art. If a venous catheter 86 is used, the infusion tip 66 will be essentially the same as disclosed above for other embodiments. The advantage here is that, in appropriate situations, the venous catheter 86 may be secured to the patient prior to the release of fluid from the fluid source 16. For example, the wings 90a-b are secured to the patient prior to the release of fluid 18 from the fluid source 16. In all other important respects, the operation of the venous catheter 86 with the infusion tip 66 of the present invention is identical to the operation disclosed previously.

Figure 7:
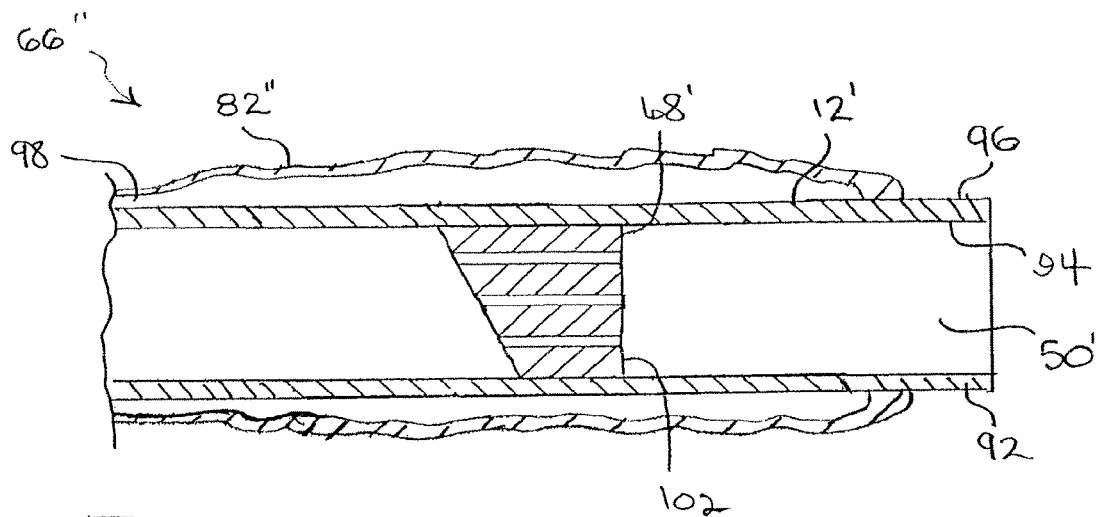
FIG. 7 is a cross-section view of an alternate embodiment of an infusion tip as seen along line 2-2 in FIG. 1, having a balloon for regulating/controlling the axial movement of a fluid (e.g. blood) past the catheter and a separator which also functions to prevent catheter tube collapse during balloon inflation, shown with the balloon in a deflated state.

FIG. 7 shows another embodiment of an infusion tip 66" having an elongated catheter 12' having a tubular-shaped wall 92 with an inner surface 94 and an outer surface 96. As shown, the inner surface 94 of the wall 92 surrounds a central lumen 50' for the catheter 12'. FIG. 7 also shows that an inflatable balloon 82" is mounted on the outer wall 96. An inflation lumen 98 is provided to selectively inflate the balloon 82" (inflated balloon 82" shown in FIG. 8). It can be seen that a portion of the outer wall 96 cooperates with the balloon 82" to establish an inflation chamber 100. To inflate the balloon 82", an inflation fluid is pumped through the inflation lumen 98, for example using the inflator 26 shown in FIG. 1 and described above, to establish a preselected inflation pressure in the inflation chamber 100. It is to be appreciated that this pressure will establish a force on the wall 92 that is directed radially inward and tends to constrict or collapse the catheter 12'. As indicated above, collapse or constriction of the catheter 12' can undesirably impede flow in the central lumen and/or stress cells such as stem cells in the central lumen flow lowering cell viability (sometimes by as much as 70-80%).

To prevent this collapse, FIG. 7 shows that the infusion tip 66" can include a reinforcing member 102 to support the catheter wall 92 under the inflatable balloon 82". As shown, for the FIG. 7 embodiment, the reinforcing member 102 is a separator 68' (as described above with reference to FIG. 3) that is positioned in the central lumen 50' under the balloon 82". Alternatively, the separator 32/68 shown in FIG. 2, the separator 68" shown in FIG. 4 or a similar separator may be positioned in the central lumen 50' under the balloon 82" to reinforce the wall 92 during inflation of the balloon 82". Functionally, the reinforcing member 102 prevents collapse of the wall 92 and maintains a substantially constant cross-section for the central lumen 50' during an inflation of the balloon 82", allowing for unimpeded fluid flow to pass through the central lumen 50' during an infusion.

Figure 8:
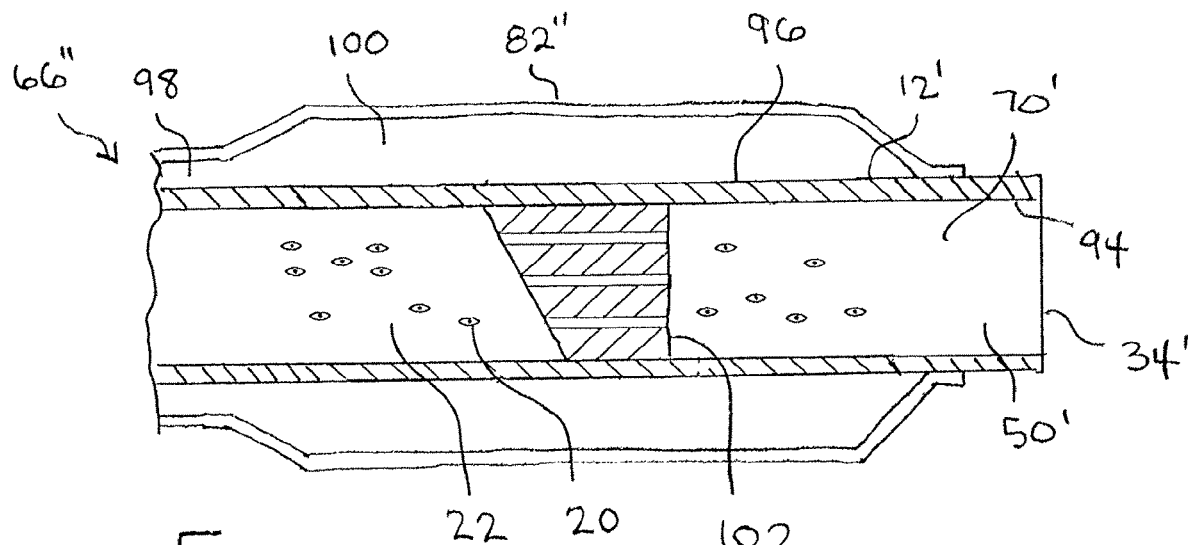
FIG. 8 is a cross-section view of the infusion tip shown in FIG. 7, shown with the balloon in an inflated state.

With the arrangement shown in FIGS. 7 and 8, the infusion tip 66" can be advanced to a treatment site suitable for delivery of particles 20 with the balloon 82" in a deflated state (as shown in FIG. 7). Next, with the infusion tip 66" at the treatment site, the balloon 82" is selectively inflated (as shown in FIG. 8) to control and/or regulate the flow of blood in the vasculature for blood flowing past the infusion tip 66". Once the blood flow (not shown) has been adequately regulated, a particle/fluid medium 22 including particles 20 can be introduced into the central lumen 50' and passed through the separator 68' to prevent large, flocculated particles from entering the bloodstream. The particle/fluid medium 22 then passes through a recollection chamber 70' and exits the distal end 34' of the catheter 12'. After the infusion, the balloon 82" can be deflated and the infusion tip 66" withdrawn from the patient's vasculature.

Figure 9:
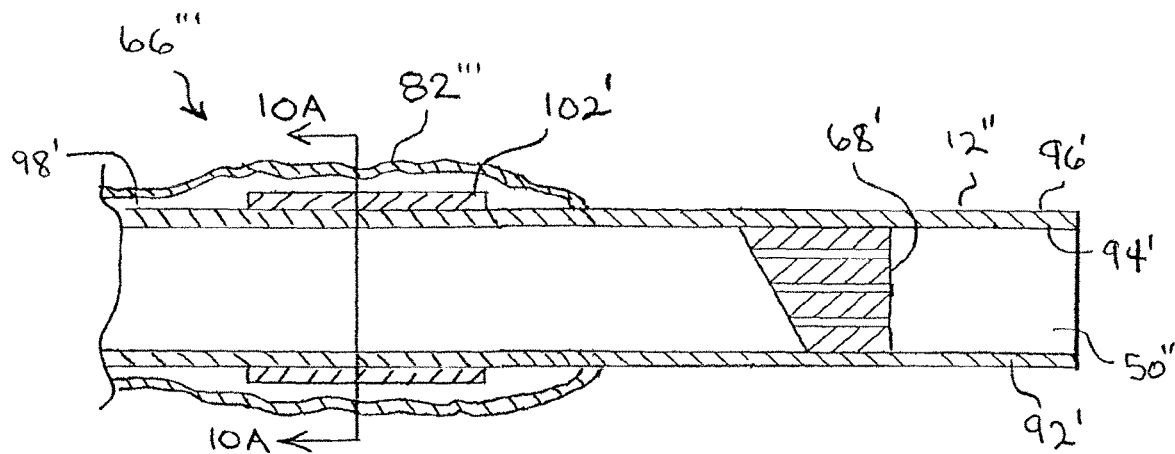
FIG. 9 is a cross-section view of an alternate embodiment of an infusion tip as seen along line 2-2 in FIG. 1, having a balloon for regulating/controlling the axial movement of a fluid (e.g. blood) past the catheter and an annular shaped ring to prevent catheter tube collapse during balloon inflation, shown with the balloon in a deflated state.
Figure 10:
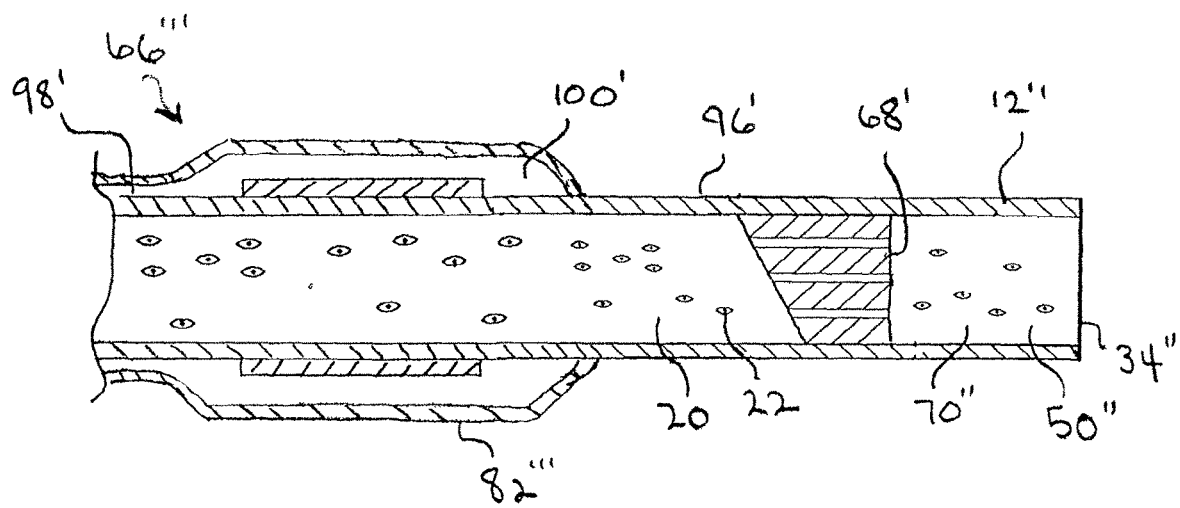
FIG. 10 is a cross-section view of the infusion tip shown in FIG. 9, shown with the balloon in an inflated state.
Figure 10A:
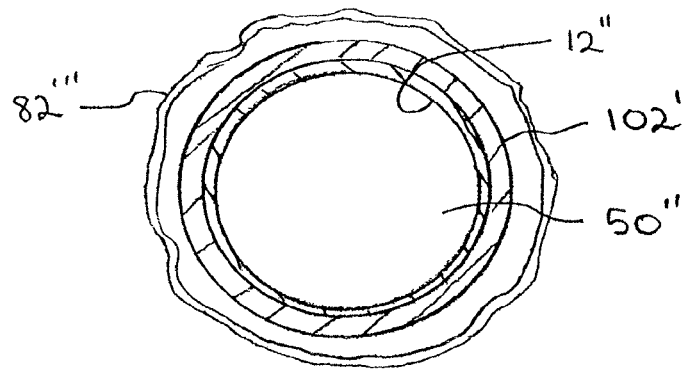
FIG. 10A is a cross-section view of the infusion tip embodiment shown in FIG. 9, as seen along line 10A-10A.

FIGS. 9, 10 and 10A show another embodiment of an infusion tip 66''' for an elongated catheter 12" having a tubular-shaped wall 92' (see FIG. 9) with an inner surface 94' and an outer surface 96'. As shown, the inner surface 94' of the wall 92' surrounds a central lumen 50" for the catheter 12". FIG. 7 also shows that an inflatable balloon 82''' is mounted on the outer wall 96'. An inflation lumen 98' is provided to selectively inflate the balloon 82''' (inflated balloon 82''' shown in FIG. 10). It can be seen that a portion of the outer wall 96' cooperates with the balloon 82''' to establish an inflation chamber 100'. To inflate the balloon 82''', an inflation fluid is pumped through the inflation lumen 98', for example using the inflator 26 shown in FIG. 1 and described above, to establish a preselected inflation pressure in the inflation chamber 100'. It is to be appreciated that this pressure will establish a force on the wall 92' that is directed radially inward and tends to constrict or collapse the catheter 12". As indicated above, collapse or constriction of the catheter 12" can undesirably impede flow in the central lumen and/or stress cells such as stem cells in the central lumen flow lowering cell viability (sometimes by as much as 70-80%).

To prevent this collapse, FIG. 9 shows that the infusion tip 66" can include a reinforcing member 102' to support the catheter wall 92' under the inflatable balloon 82"'. As shown, for the FIG. 9 embodiment, the reinforcing member 102' can be formed as an annular shaped ring that is affixed to the outer surface 96' of the catheter wall 94' under the balloon 82"'. Once affixed, the ring shaped reinforcing member 102' is oriented substantially perpendicular to a longitudinal axis 42' defined by the infusion catheter 12", as shown. Functionally, the reinforcing member 102' prevents collapse of the wall 92' and maintains a substantially constant cross-section for the central lumen 50" during an inflation of the balloon 82"', allowing for unimpeded fluid flow to pass through the central lumen 50" during an infusion.

With the arrangement shown in FIGS. 9 and 10, the infusion tip 66"' can be advanced to a treatment site suitable for delivery of particles 20 with the balloon 82"' in a deflated state (as shown in FIG. 9). Next, with the infusion tip 66"' at the treatment site, the balloon 82"' is selectively inflated (as shown in FIG. 10) to control and/or regulate the flow of blood in the vasculature for blood flowing past the infusion tip 66". Once the blood flow (not shown) has been adequately regulated, a particle/fluid medium 22 including particles 20 can be introduced into the central lumen 50" and passed through the separator 68' to prevent large, flocculated particles from entering the bloodstream. Alternatively, the separator 32/68 shown in FIG. 2, the separator 68" shown in FIG. 4, or a similar separator may be used. The particle/fluid medium 22 then passes through a recollection chamber 70" and exits the distal end 34" of the catheter 12". After the infusion, the balloon 82"' can be deflated and the infusion tip 66"' withdrawn from the patient's vasculature.

Figure 10B:
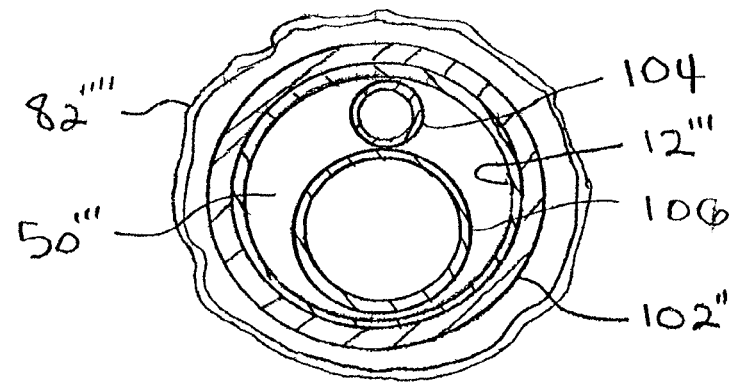
FIG. 10B is a cross-section view as in FIG. 10A showing another infusion tip embodiment having an inflation tube and infusion tube within the central lumen of the catheter.

FIG. 10B shows another infusion tip embodiment having an inflation tube 104 and an infusion tube 106 positioned within the central lumen 50"' of the catheter 12"'. For this embodiment, an inflatable balloon 82"' is mounted on the catheter 12"', and is connected in fluid communication with the inflatable balloon 82"'. To prevent a collapse of the catheter 12"' during inflation of the balloon 82"', a reinforcing member 102" is provided to support the catheter 12"'. Collapse of the catheter 12"' during inflation may constrict the infusion tube 106 and undesirably impede flow in the infusion tube 106 and/or stress cells, such as stem cells in the infusion tube 106, lowering cell viability. As shown, for the FIG. 10B embodiment, the reinforcing member 102" can be formed as an annular shaped ring that is affixed to the outer surface of the catheter 12"' under the balloon 82"'.

Figure 11:
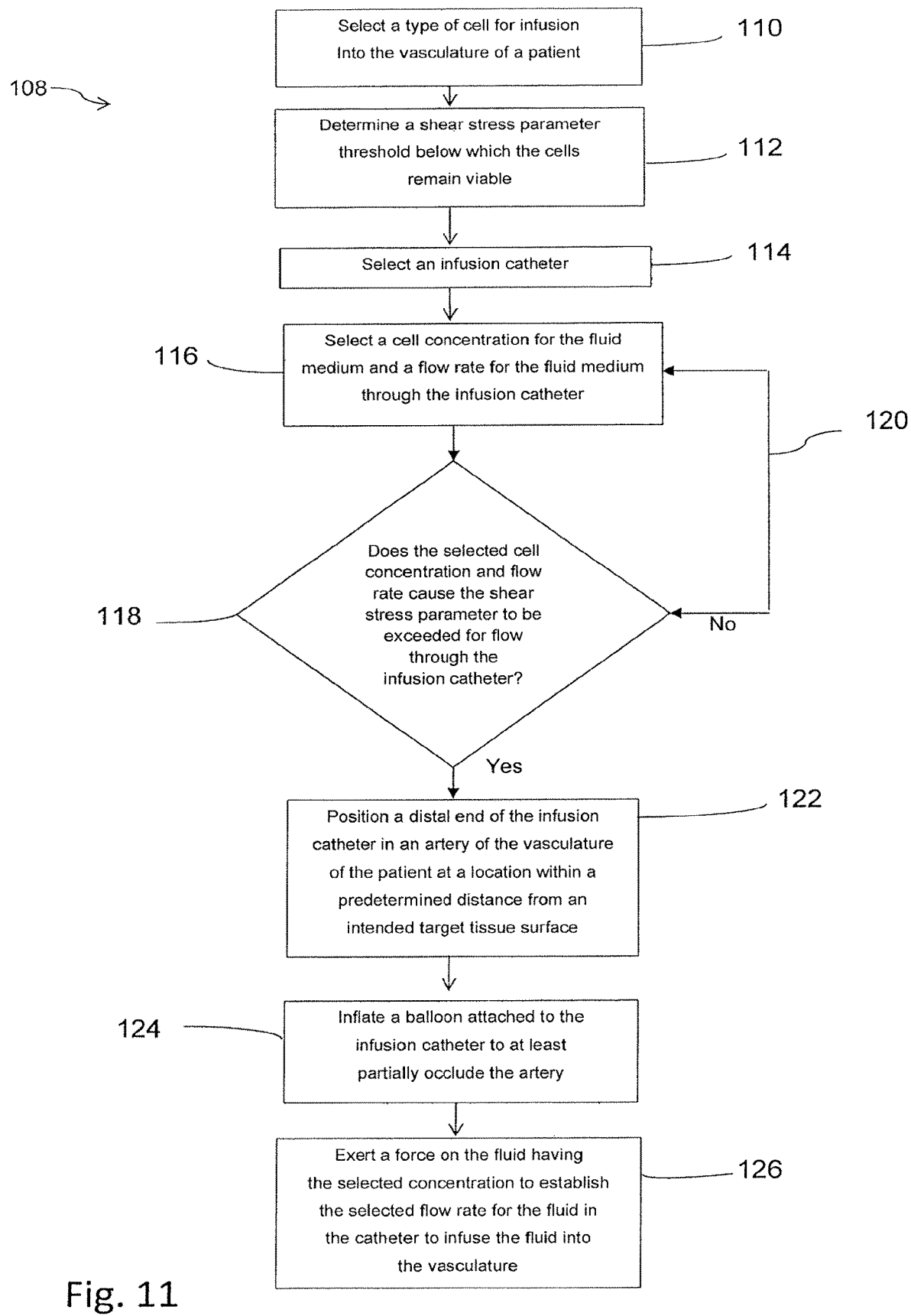
FIG. 11 is a flow-chart illustrating a protocol for infusing cells, such as stem cells, which ensures that stresses exerted on the cells are maintained below a shear stress threshold specified for the type of cell to prevent cell damage during an infusion procedure.

FIG. 11 shows a protocol 108 for infusing cells, such as stem cells, which ensures that stresses exerted on the cells are maintained below a shear stress threshold specified for the specific type of cell to prevent cell damage during an infusion procedure. As shown, the protocol begins by selecting a type of cell or cell family for infusion into the vasculature of a patient during a treatment procedure (Box 110). Next, for the cell or cell family selected, a shear stress parameter threshold below which the cells remain viable is determined (Box 112). For example, this determination can be made experimentally. In some types of cells, the shear stress parameter can be a maximum shear stress. For other types of cells, both the magnitude of the shear stresses and the time the cell is exposed to the shear stress can be considered when establishing the shear stress threshold.

Continuing with reference to FIG. 11, it can be seen that for the protocol 108, an infusion catheter is selected (Box 114). For example, the infusion catheter can include internal multi-lumen separator to de-flocculate cells, such as the separator 68' shown in FIG. 10, and/or an inflation balloon, such as the balloon 82"' shown in FIG. 10. For the protocol 108, the size, shape and arrangement of the internal passages in the infusion catheter may affect the shear stresses developed for a fluid flowing through the catheter. In addition, for cases in which the passages change size or constrict due to balloon inflation, these changes can be considered in the protocol 108 when estimating the shear stresses that develop for a fluid flowing through the catheter.

Box 116 shows that a cell concentration for the fluid medium and a flow rate for the fluid medium through the infusion catheter can be selected with the understanding that each of these selections may affect the shear stresses developed for a fluid flowing through the catheter. For example, the concentration of cells in the fluid can affect the fluid's viscosity, which in turn, can affect the flow of the fluid through the catheter and ultimately the shear stresses that develop for a fluid flowing through the catheter.

As shown in Box 118, once an initial cell concentration and flow rate have been selected, a shear stress parameter can be measured or calculated and compared with the shear stress threshold determined in Box 112. If the measured or calculated shear stress parameter exceeds the shear stress threshold determined in Box 112, arrow 120 indicates that a new cell concentration and flow rate is then selected (Box 116). This selection (Box 116) and comparison (Box 118) can be repeated, as needed, until the measured or calculated shear stress parameter does not exceed the shear stress threshold determined in Box 112.

Next, for the protocol 108, as shown in Box 122, a distal end of the infusion catheter can be positioned in an artery of the vasculature of the patient at a location within a predetermined distance from an intended target tissue surface. With the catheter properly positioned, Box 124 indicates that the next step in the protocol 108 is to inflate the catheter balloon to at least partially occlude the artery. In this manner, blood flow past the distal end of the catheter can be reduced to increase the efficacy of the infusion procedure. With the catheter properly positioned and the balloon inflated, Box 126 shows that a force can then be exerted on the fluid to establish the selected flow rate for the fluid in the catheter to infuse the fluid into the vasculature. For example, a suitable flow rates for the liquid are in the range of 3 milliliters/minute to 12 milliliters/minute and a suitable concentration of stem cells in the liquid is in the range of about $4 \times 10^6$ cells/milliliter to about $6 \times 10^6$ cells/milliliter.

While the particular Method for Infusing Stem Cells as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for infusing a liquid into the vasculature of a patient which comprises the steps of:
   supplying a source of the liquid;
   providing an infusion catheter, wherein the infusion catheter has a proximal end and a distal end and is formed with a multi-lumen infusion unit mounted adjacent the distal end of the infusion catheter, and wherein the infusion catheter includes an inflation balloon affixed to the infusion catheter proximal to the multi-lumen infusion unit;

positioning the distal end of the infusion catheter in an artery of the vasculature of the patient at a location within a predetermined distance from an intended target tissue surface;

inflating the inflation balloon to at least partially occlude the artery; and exerting a force on the liquid to establish a flow rate for the liquid in the infusion catheter to infuse the liquid from the infusion catheter through the multi-lumen infusion unit and into the vasculature with a homogeneous distribution of the liquid to cover the surface of the intended target tissue, wherein the flow rate is established in accordance with an infusion protocol, and the infusion protocol is characterized by time and liquid volume parameters based on viscosity and pressure values in the liquid; and wherein the liquid comprises a fluid medium having a suspension of cells.

2. A method as recited in claim 1 wherein the force is exerted on the liquid to provide a substantially constant shear-stress distribution in the liquid during an infusion.

3. A method as recited in claim 1 wherein the force is exerted on the liquid to provide a substantially homogeneous distribution of cells suspended in the liquid during an infusion.

4. A method as recited in claim 1 wherein the suspension of cells is a suspension of stem cells.

5. A method as recited in claim 1 wherein the force establishes the flow rate for the liquid in the range of 3 milliliters/minute to 12 milliliters/minute.

6. A method as recited in claim 4 wherein the concentration of stem cells in the fluid medium is in the range of $4 \times 10^6$ cells/milliliter to $6 \times 10^6$ cells/milliliter.

7. A method for infusing a fluid medium having a suspension of cells into the vasculature of a patient, the method comprising the steps of:

determining a shear stress parameter threshold below which the cells remain viable;

providing an infusion catheter having an internal multi-lumen separator to de-flocculate cells;

selecting a cell concentration for the fluid medium and a flow rate for the fluid medium through the infusion catheter to cause the fluid medium to flow through the infusion catheter without exceeding the shear stress parameter threshold;

positioning a distal end of the infusion catheter in an artery of the vasculature of the patient at a location within a predetermined distance from an intended target tissue surface;

inflating a balloon attached to the infusion catheter to at least partially occlude the artery; and exerting a force on the fluid medium having the selected concentration to establish the selected flow rate for the fluid medium in the infusion catheter to infuse the fluid medium from the infusion catheter through the internal multi-lumen separator and into the vasculature with a homogeneous distribution of the fluid medium towards the intended target tissue surface without exceeding the cell viability shear stress parameter threshold, wherein the flow rate is established in accordance with an infusion protocol, and the infusion protocol is characterized by time and fluid medium volume parameters based on viscosity and pressure values in the fluid medium.

8. A method as recited in claim 7 wherein the shear stress parameter threshold is a maximum shear stress threshold.

9. A method as recited in claim 7 wherein the shear stress parameter threshold is a time that a cell is above a selected shear stress.

10. A method as recited in claim 7 wherein the suspension of cells is a suspension of stem cells.

11. A method as recited in claim 10 wherein the force establishes the flow rate for the liquid in the range of 3 milliliters/minute to 12 milliliters/minute.

12. A method as recited in claim 10 wherein the concentration of stem cells in the fluid medium is in the range of $4 \times 10^6$ cells/milliliter to $6 \times 10^6$ cells/milliliter.

13. A method as recited in claim 7 wherein the internal multi-lumen separator has a plurality of parallel lumens and is positioned in the infusion catheter at a distance, d, from the distal end of the infusion catheter to establish a recollection chamber at the distal end of the infusion catheter.

14. A method for infusing a fluid medium having a suspension of cells into the vasculature of a patient, the method comprising the steps of:

providing an infusion catheter having an internal multi-lumen separator to de-flocculate cells;

positioning a distal end of the infusion catheter in an artery of the vasculature of the patient at a location within a predetermined distance from an intended target tissue surface;

inflating a balloon attached to the infusion catheter to at least partially occlude the artery; and flowing the fluid medium having a selected cell concentration through the infusion catheter and through the internal multi-lumen separator at a flow rate for the fluid medium to cause the fluid medium to flow through the infusion catheter without causing cell damage due to shear stress.

15. A method as recited in claim 14 wherein the suspension of cells is a suspension of stem cells.

16. A method as recited in claim 15 wherein the flow rate is established in accordance with an infusion protocol, and the infusion protocol is characterized by time and fluid medium volume parameters based on viscosity and pressure values in the fluid medium; wherein the step of flowing the fluid medium establishes the flow rate for the fluid medium in the range of 3 milliliters/minute to 12 milliliters/minute; and wherein the flowing includes flowing a homogeneous distribution of the fluid medium into the artery towards the intended target tissue surface.

17. A method as recited in claim 15 wherein the flow rate is established in accordance with an infusion protocol, and the infusion protocol is characterized by time and fluid medium volume parameters based on viscosity and pressure values in the fluid medium; wherein the concentration of stem cells in the fluid medium is in the range of $4 \times 10^6$ cells/milliliter to $6 \times 10^6$ cells/milliliter; and wherein the flowing includes flowing a homogeneous distribution of the fluid medium into the artery towards the intended target tissue surface.

18. A method as recited in claim 14 wherein the internal multi-lumen separator has a plurality of parallel lumens and is positioned in the infusion catheter at a distance, d, from the distal end of the infusion catheter to establish a recollection chamber at the distal end of the infusion catheter.

19. A method as recited in claim 14 wherein the flow rate is established in accordance with an infusion protocol, and the infusion protocol is characterized by time and fluid medium volume parameters based on viscosity and pressure values in the fluid medium.

* * * * *